Figure 3:
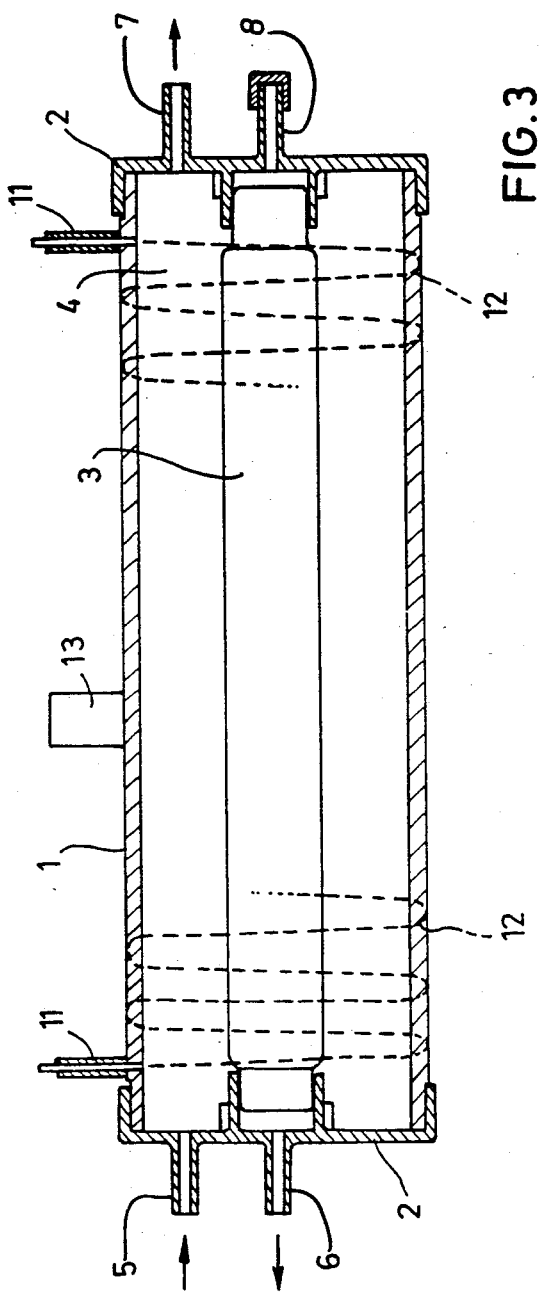

United States Patent [19]
Rosskopf et al.

[11] Patent Number: 4,648,974
[45] Date of Patent: Mar. 10, 1987

[54] PROCESS FOR THE SELECTIVE EXTRACORPOREAL SEPARATION OF BLOOD CONSTITUENTS

[75] Inventors: Gerhard Rosskopf, Fuldabruck-Dornhagen; Dietrich Seidel, Gottingen; Heinrich Wieland, Waake, all of Fed. Rep. of Germany

[73] Assignee: Intermedicat GmbH, Emmenbrucke, Switzerland

[21] Appl. No.: 589,462

[22] Filed: Mar. 14, 1984

[30] Foreign Application Priority Data

Mar. 24, 1983 [DE] Fed. Rep. of Germany ....... 3310727

[51] Int. Cl.⁴ ............................................. B01D 13/00
[52] U.S. Cl. ................................. 210/651; 210/323.2; 210/433.2; 210/737; 210/774; 210/805; 210/927
[58] Field of Search ..................... 210/639, 649–651, 210/737, 774, 177, 186, 433.2, 927, 433.1, 323.2, 805

[56] References Cited

U.S. PATENT DOCUMENTS

| | | | |
|---|---|---|---|
| Re. 31,688 | 9/1984 | Popovich et al. | 210/927 X |
| 3,074,402 | 1/1963 | Broman | 210/927 X |
| 3,722,680 | 3/1973 | Smith | 210/186 X |
| 3,809,241 | 5/1974 | Alvine | 210/186 X |
| 4,267,053 | 5/1981 | Hashino et al. | 210/650 |
| 4,303,530 | 12/1981 | Shah et al. | 210/651 |
| 4,317,775 | 3/1982 | Burri et al. | 424/271 X |
| 4,350,156 | 9/1982 | Malchesky et al. | 210/651 X |

OTHER PUBLICATIONS

Kambic, et al., Plasmapheresis Historical Perspective Therapeutic Applications and New Frontiers, pp. 67–83.
Lysaght, et al., "Contemporary Technical Issues in Plasmapheresis: Controversies and Reconciliation" Plasma Separation and Plasma Fractionation, pp. 315–328, (1983).
Malchesky, et al., "Cryoprocesses for Macromolecule Separation" Plasma Separation and Plasma Fractionation, pp. 200–212 (1983).
Malchesky, et al., "Discussion . . ." Plasma Separation and Plasma Fractionation, pp. 218–222 (1983).
Microfiltration Products Division, Specification Bulletin for Zetapor SP0.20 μm, Pharmaceutical Trade Cartridge, Zm. 10.6, (9/15/83).
Ultrareine Flüssigkeiten Mikrofiltration, Specification Bulletin for Forschungsinstitut Berghof GmbH 74 Tübingen-1, (1980).
"Membrane Separation Processes for Macromolecule Removal", Malchesky, et al., Plasmapheresis ISAO Press (1983), pp. 51–66.
Gurland, et al., "Clinical Applications of Macromolecular Separations", Trans. Am. Artif. Intern Organs, vol. XXVII, (1981), pp. 356–363.

Primary Examiner—Richard V. Fisher
Assistant Examiner—W. Gary Jones
Attorney, Agent, or Firm—Kenyon & Kenyon

[57] ABSTRACT

The invention relates to processes and apparatus employing filter candles with an effective filter surface area of 0.2 to 2 square meters and a mean pore diameter of 0.2 to 2 micron in sterilizable cylindrical housings for the selective extracorporeal separation of precipitates of macromolecular pathologic and/or toxic species from blood or blood constituents, such as whole serum or plasma.

19 Claims, 3 Drawing Figures

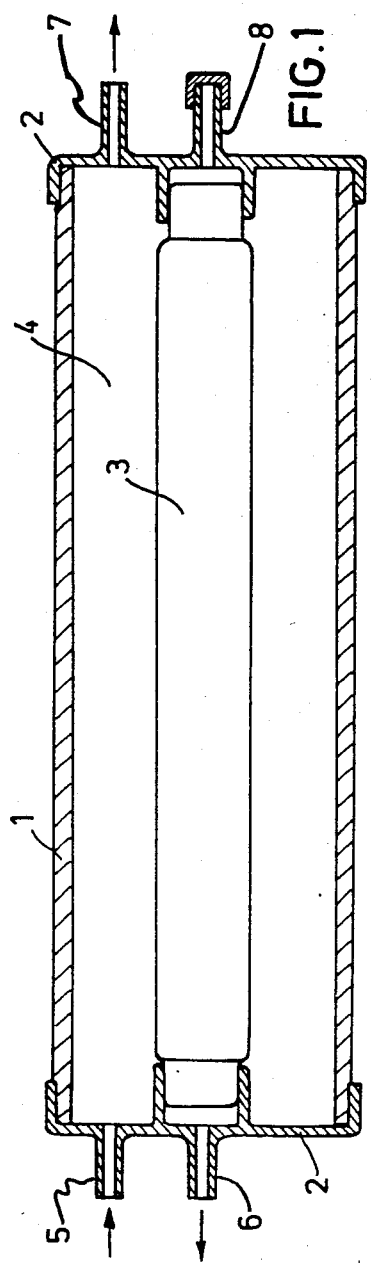
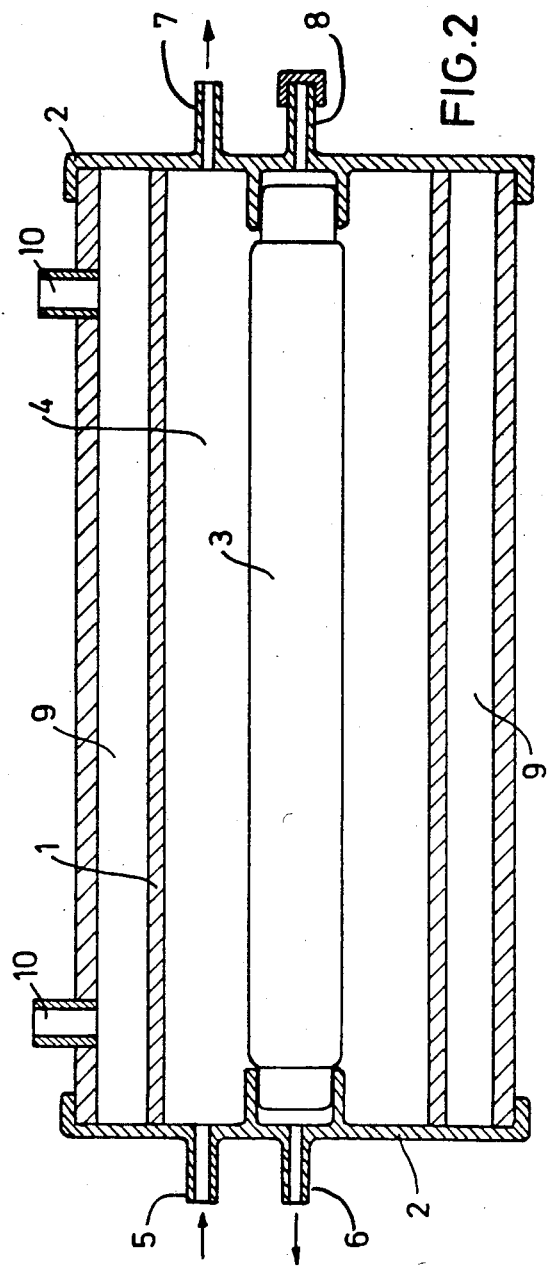

PROCESS FOR THE SELECTIVE EXTRACORPOREAL SEPARATION OF BLOOD CONSTITUENTS

The invention relates to a method and apparatus, employing a filter candle, for the selective extracorporeal separation of pathologic and/or toxic blood constituents.

Progress made in recent years in the field of analysis of the lipoprotein system of the human body has shown that a high plasma cholesterol concentration, and hence the risk of early arteriosclerosis, specifically coronary sclerosis, is attributable essentially to the presence of high concentrations of high-cholesterol beta-lipoproteins in the body. In human blood normally about 70 to 80% of the total cholesterol is bound to beta-lipoproteins (low density lipoproteins, referred to as LDL). In morbid processes which are accompanied by a disturbed lipo-metabolism or respectively elevated plasma lipid concentrations, the percentage of LDL-combined cholesterol in the total cholesterol may rise even higher. As a rule, therefore, hypercholesterolemia is brought about by hyper-beta-lipoproteinemia.

Therapeutic efforts to effectively lower the beta-lipoprotein concentrations have heretofore been unsatisfactory Especially in the genetic forms of lipo-metabollic disorders, control by medication is extremely difficult.

Two methods have been tried heretofore, for mechanically separating beta-lipoproteins from blood: elimination of LDL from blood by means of specific antibodies that are coupled to a matrix; and complete exchange of the entire blood serum by plasmapheresis.

The antibodies used for the first method were obtained by immunizing sheep or rabbits. This method (W. Stoffel and Th. Demant, Selective Removal of Apolipoprotein B-Containing Serum Lipoproteins from Blood Plasma, Proc. Nat. Acad. Sci., U.S.A., 78, 611–615 (1981)) has the disadvantage of low efficiency, which has already led to a modification of the treatment procedure by this method. In addition, there is danger, theoretically, that the use of antibodies produced in an animal might in the long run cause immunological problems in the person being treated.

In plasmapheresis, which involves a complete exchange of the entire blood serum, the beta-lipoprotein content of the affected patient is indeed lowered, but under the conventional methods, due to their particular instrumentation, those lipoproteins (i.e., high density lipoproteins, HDL) which counteract arteriosclerosis are also eliminated concurrently. Moreover, all other proteins of the plasma, including coagulation factors, globulins and hormones, are eliminated as well. However, until now, this method has proved useful for very specific cases of hyper-beta-lipoproteinemia.

In order to remove beta-lipoproteins from the blood or blood plasma selectively and at high capacity, the corpuscular constituents of the blood are separated by known methods, for instance, as described in co-pending U.S. patent application Ser. No. 414,809, filed Sept. 3, 1982, and the remaining plasma is mixed with heparin in a suitable buffer, e.g., an acetate-citrate buffer, the beta-lipoprotein-heparin complex which thereafter forms being precipitated at the isoelectric point at a pH of 5.05 to 5.25 and subsequently removed.

Numerous other diseases are also accompanied by a rise in the content of antibodies or of macromolecular species of a pathogenic nature, the concentrations of which also have been lowered successfully by plasmapheresis. To this end, the toxic species are removed selectively by precipitation. Examples of such species are globulins, such as the rheumatic factor, Bence-Jones factors and also other pathogenic macromolecules.

Several methods have been described for the separation of such high molecular weight species from blood plasma. Thus, Swiss patent No. 626,256 discloses an apparatus for the continuous extracorporeal separation of such substances from the blood. This apparatus consists of a filtering device containing a medium which adsorbs the macromolecular species. The adsorber contains insolubilized enzymes, antigens or antibodies, but it is incapable of selective separation of certain species present along with related ones also existing in the plasma, especially under non-physiological conditions as they occur in cryoprecipitation or after denaturation by heat.

Filtration methods using membrane or capillary filters have been described, e.g., in European Patent EP-A No. 0,041,350. In a so-called filtration cascade, the plasma which contains the macromolecules is separated from the blood in a first filtering stage, and then, in a second filtration stage, the macromolecules are removed therefrom at a physiological temperature or under cooling. The nominal pore diameter of the second membrane is stated to be 0.01 to 0.2 micron.

The disadvantage of such membrane and capillary filters is that, for the separation of larger quantities of precipitates, their surfaces are too small and, for reasons of membrane stability, their pore diameters are too small. In addition, such filters clog very quickly with the precipitates and with entrained fibrin, especially if the filtration takes place under pressure. This often necessitates a filter change in the extracorporeal circulation system, with all the medical and technical complications incident thereto.

The invention described herein has as an objective a process and apparatus which permit removing pathologic and/or toxic species of relatively high molecular weight from the blood, i.e., from whole serum or from constituents of the blood such as plasma, selectively and with a high capacity, in an extracorporeal circulation system. Here filters should be used which, after selection of a suitable and widely variable pore width, completely retain relatively large quantities of precipitates from a large quantity of plasma, offer little resistance to the plasma, and do not clog in the course of the filtration process.

The objective is achieved by the use of filter candles in a process and apparatus suitable for the separation of the named species.

The invention relates to a process for the selective, extracorporeal separation of precipitates, such as are produced by addition of precipitation agents and/or chemical reagents or denaturation by cooling or heating, of macromolecular pathologic and/or or toxic species from blood or blood constituents such as whole serum or plasma. Characteristically, it employs a plasma fraction which has been produced by a capillary or membrane plasma filter or the last filter of a cascade of several such filters with molecular exclusion limits of 50,000 to 3,000,000 Dalton continuously from patient blood or fractions thereof, and which plasma fraction contains precipitates of macromolecular pathologic or toxic species produced by addition of precipitation agents and/or chemical reagents or by denaturation by cooling or heating. The process comprises passing such a plasma fraction at atmospheric pressure through a cylindrical sterilized housing comprising a filter candle, the filter candle having a filtration means and an inner core, and being installed in a closed extracorporeal circulation system, whereby such plasma fraction sweeps the filtration means externally and whereby plasma purified by filtering passes into the interior core and the precipitates are retained in or on the filtration means; discharging the purified plasma from the core; and returning purified plasma to a patient.

The invention also relates to apparatus for the selective extracorporeal separation of precipitates of macromolecular pathologic or toxic species from blood or blood constituents. The apparatus comprises a filter candle having an effective filter surface in the range of from about 0.2 to about 2 square meters, a mean pore diameter in the range of from about 0.2 to about 2 micron, the filter candle also having an internal core, and being disposed in a sterilizable cyclindrical housing made of plastic or glass. The housing is provided with at least one filtrate outlet adapted to permit drainage of fluid filtrate from the core, and with a first inlet located at one end of the housing and adapted to permit introduction of blood or a fraction thereof. Such first inlet is located between the outer radius of the core and the inner radius of the housing.

In a further embodiment, the invention comprises, in a process for the selective extracorporeal separation of precipitates of macromolecular pathologic and/or toxic species from blood or blood constituents, such as whole serum or plasma, the improvement of employing a filter candle having an effective filter surface in the range of from about 0.2 to about 2 square meters, a length in the range of from about 10 to about 60 cm, and a mean pore diameter in the range of from about 0.2 to about 2 micron, disposed in a sterilizable cylindrical housing.

The filter candles employed in practicing the invention are commonly used in technical filtration processes, e.g., in the purification of drinking water and the production of ultra-pure water for special purposes. They have a mean pore diameter in the range from about 0.2 to about 2 micron, preferably in the range from about 0.4 to about 1 micron, which enables them on the one hand to completely retain the precipitated pathologic and/or toxic species as precipitates, while on the other hand offering virtually no resistance to the plasma.

The effective filter surface of the filter candles used is in the range from about 0.2 to about 2 square meters, preferably in the range of from about 0.8 to about 1.7 square meters, depending on the length of the filter candles used, which typically is in the range of from about 10 to about 60 cm. The filter candle should be of the same length as the housing in which it is disposed. Such large surfaces are found to be suitable for absorbing, without clogging, the entire precipitates from 2 liters of plasma, which is a typical quantity of a purification run in a patient.

According to the invention, all filter candles which meet the requirements referred to herein may be employed. A specific filter candle which has been employed is sold under the trademark NUCLEPORE QR, the filtration medium of which consists of a polycarbonate membrane.

Referring now to the drawings, apparatus according to the invention is depicted in:

FIG. 1, which shows the apparatus as it is employed, for example, for the separation of precipitates of low-density lipoproteins precipitated with heparin at room temperature from blood or blood plasma;

FIG. 2, which shows a preferred embodiment suitable for the precipitation and subsequent separation of pathologic or toxic blood constituents at low or elevated temperature; and FIG. 3, which shows an additional preferred embodiment as used in the separation of precipitates precipitated after denaturation by heat.

The apparatus of the invention for the selective extracorporeal separation of the precipitates from blood or blood plasma, which can be installed as a filter section in a cascade filtration system, consists of a cylindrical housing 1, which may be fabricated of plastic or glass, and which is, as depicted, threaded at its upper and lower ends. At the upper and lower ends, the cylinder is closed by internally threaded covers 2, which by means of ultrasonic welding may be hermetically and sterilely sealed. The cylindrical housing 1 contains a filter candle having an interior core 3 and a filter body 4. The covers 2 are provided with filtrate outlets 6, 8. As depicted, outlet 6 is adapted for the withdrawal of the filtrate, i.e., the plasma which has been filtered, and outlet 8 is capped. Typically, filtrate outlets 6, 8 are co-axial with core 3, but this is not essential. One cover 2 is provided with a first inlet 5, adapted for the introduction of the plasma fraction to be filtered. The other cover is provided with an outlet 7, adapted for the withdrawal of excess plasma and suspended solids. Inlet 5 and outlet 7 are located between the outer radius of core 3 and the inner radius of housing 1. Core 3 and filter body 4 should exactly match the interior volume of the housing as to dimensions, and should be glued tightly into the housing 1 in such a way that the core 3 lies between filtrate outlets 6, 8, while the filter body 4 lies at the levels of inlet 5 and outlet 7.

Referring now to FIG. 2, which depicts apparatus especially adapted for cryoprecipitation or heat denaturation, housing 1 is surrounded by a thermostatically-controlled jacket 9, through which any desired cooling or heating fluid can be conducted via inlet and outlet ports 10.

Referring now to FIG. 3, housing 1 may be heated by means of heating wires 12, to achieve denaturation by heat constituents contained in the plasma. Current is supplied to the heating wires 12 via two plug contacts 11 which are disposed to permit, just like mounting coupling 13, direct electrical plugging of the filter housing 1 into, for example, a monitor.

The filter candles and the apparatus described according to the invention, as well as the connections to the remainder of the circulation system for extracorporeal separation of precipitates from blood or blood plasma, are designed so as to permit working under sterile conditions, which is imperative in such cases. This requires that all materials be selected so as to permit sterilization under the usual conditions.

An essential advantage of the process of the invention over the methods known in the prior art is that, by comparison with capillary filters, no lateral drain nipple at the cylinder jacket for withdrawing the purified plasma by means of a vacuum is necessary. Due to the structural design of the filter candles, the plasma supplied through inlet 5 sweeps the filter surface of filter candle 4 externally. The filtrate penetrates into the interior core 3 by gravity alone, without application of an external vacuum, and is conducted away via outlet 6. The precipitate remains in the fabric of the filter. That portion of the plasma which is not filtered off by gravity can be removed via outlet 7, and, if desired, may be recirculated by combining it with fresh plasma being introduced via outlet 5. Outlet 8 then remains closed. Thus, the process operates at the ambient atmospheric pressure, without the need for applying a pressure differential across the filtration means.

If, for instance to remove the rheumatic factor, the plasma is to be cooled to a low temperature during cryoprecipitation in order to achieve precipitation of the species to be separated, a suitable temperature-controlling liquid, preferably water, may be introduced via inlet port 10 into the thermostatically-controlled jacket 9, as shown in FIG. 2, with the result that the plasma is cooled to a temperature preset by a thermostat. The filtered plasma, which is withdrawn via outlet 6, must then be warmed to body temperature again before being returned into the patient's blood circulation.

For the separation of blood plasma constituents precipitated by heat denaturation, e.g., Bence-Jones factors, the apparatus of FIG. 3 may be employed. Current is supplied to the heating wires 12 via plug contacts 11; the temperature can be controlled exactly by means of a regulating system (not shown). The purified plasma withdrawn through outlet 6 must be cooled accordingly to body temperature before being returned into the patient circulation.

The further advantages of the method of the invention therefore reside in that, depending on the specific requirements of the particular separating process, very specific, controlled conditions can be set and maintained, without giving up the other advantages of the method, namely an almost pressureless filtration via filter systems with a very large surface without danger of obstruction of the filters and all the complications connected therewith.

The invention is exemplified by the following examples.

EXAMPLE 1

The blood of a patient with hereditary hypercholesterolemia (homozygote) with a starting cholesterol value of 416 mg/dl or, respectively, an LDL cholesterol value of 368 mg/dl, was to be purified from beta-lipoproteins.

There was used a simple cylinder housing according to FIG. 1 which contained a filter candle of a mean pore diameter of 0.4 micron, sold under the trademark NUCLEPORE QR.

Two liters of the patient's blood plasma were diluted in the volumetric ratio 1:1 with 2 liters of 0.2 M sodium acetate buffer (pH: 4.86) which contained 50,000 units per liter of heparin, which resulted a pH value of the mixture of 5.12.

The heparin-buffer-plasma mixture was subjected to the method of the present invention, whereby the plasma was completely purified from low-density lipoproteins within 30 minutes.

Despite this concentration of LDL, found only in rare cases, and the volume of plasma, there was no observed pressure increase at the filter. The filter remained clear to the end. At no time did the clear filtrate contain low-density lipoproteins.

EXAMPLE 2

In accordance with Example 1, plasma from patient blood which contained the rheumatic factor and "$C_{1q}$ binding immune complexes" was subjected to cryoprecipitation. To this end, the plasma was introduced into apparatus constructed according to FIG. 2, the thermostatically-controlled jacket having been cooled to 4° C. The filter candle had a mean pore diameter of 0.4 micron, sold under the trademark NUCLEPORE QR. After filtration, the purified plasma contained less than 5% of the originally present rheumatic factors and "$C_{1q}$ binding immune complexes"

EXAMPLE 3

The separation of Bence-Jones factors from blood plasma was conducted after denaturation by heating to 50° C. in apparatus constructed according to FIG. 2, the thermostatically-controlled jacket of which had been heated to 50° C. The filter candle had a mean pore diameter of 0.4 micron, sold under the trademark NUCLEPORE QR. After filtration, the plasma was free from denaturation products. No obstruction of the filter was observed.

EXAMPLE 4

The separation of Bence-Jones factors from blood plasma was conducted after denaturation by heating to 50° C. in apparatus constructed according to FIG. 3. The filter candle had a mean pore diameter of 0.4 micron, sold under the trademark NUCLEPORE QR.

After filtration, the plasma was free from denaturation products. No obstruction of the filters was observed While the processes and apparatus described herein constitute preferred embodiments of the invention, it is to be understood that there are variations in materials and equipment which may be employed which included in the invention as define by the appended claims. Therefore, the detailed description should be considered illustrative rather than as restrictive.

Having thus described the invention, what is claimed is:

1. A process for the selective exteracorporeal separation of precipitates of macromolecular pathologic or toxic species from blood having serum and plasma constituents, which comprises passing the serum or plasma through a housing comprising a filter candle defining a filter body and further defining a filtering means having an inner core, said filtration means longitudinally disposed therein and providing for the collection of filtrate and the exclusion of precipitate, said housing further having an inlet and outlet in communication with said filter body and said filtering means having an effective filter surface in the range of from about 0.2 to about 2 square meters, a length in the range of from about 10 to about 60 cm, and a means pore diameter in the range of from about 0.2 to about 2 micron.

2. The process of claim 1, wherein said filter candle has an effective filter surface in the range of from about 0.8 to about 1.7 square meters, a length in the range of from about 10 to about 50 cm, and a mean pore diameter in the range of from about 0.4 to about 1 micron.

3. The process of claim 1, wherein said housing is made of plastic or glass.

4. A process for the selective extracorporeal separation of precipitates of macromolecular pathologic or toxic species from a plasma fraction which has been produced by a filter or the last filter of a cascade of several filters with molecular exclusion limits of 50,000 to 3,000,000 Dalton continuously from patient blood or fractions thereof, and which plasma fraction contains precipitates of macromolecular pathologic or toxic species, which process comprises introducing said plasma fraction at atmospheric pressure through a housing comprising a filter candle, said filter candle comprising a permeable filtration means having an inner core, said filtration means longitudinally disposed within a filter body defined by said filter candle, and is installed in a closed extracorporeal circulation system, whereby said plasma fraction sweeps said filtration means externally and plasma purified by filtering passes into said core, said precipitates being prevented from entering into said core and said purified plasma from said core is returned to a patient.

5. The process of claim 4, which also comprises removing excess reagents from said purified plasma or adjusting the temperature thereof prior to returning said purified plasma to said patient.

6. The process of claim 4, which also comprises maintaining said plasma at body temperature in a cylindrical housing fabricated from plastic or glass.

7. The process of claim 4, which also comprises maintaining said plasma during filtration at temperatures in the range of from below body temperature to about 4° C.

8. The process of claim 4, which also comprises maintaining said plasma during filtration at temperatures from above body temperature to about 60° C.

9. The process of claim 4, wherein said filtering means has an effective filtering surface in the range of from about 0.2 to about 2 square meters, a length in the range of from about 10 to about 60 cm, and a mean pore diameter in the range of about 0.2 to about 2 micron.

10. The process of claim 4, wherein any portion of the plasma which is not filtered off by gravity is conducted out of said housing and is recirculated to the stream of fresh plasma being introduced into said housing.

11. A process for the selective exteracorporeal separation of precipitates of macromolecular pathological and toxic species from blood having serum and plasma constituents which comprises passing the serum or plasma through a housing having an inlet and outlet comprising a filter candle defining a filter body in communication with said inlet and further defining a permeable filtering means having an inner core in communication with the outlet longitudinally disposed within said filter body and having pores which exclude the precipitates from entering the inner core, and through which filter body the serum or plasma is passed such that the serum or plasma enters one end of the filter body through the inlet and contacts the filtering means through which is passed filtrate from the plasma or serum, excluding the precipitate.

12. The process according to claim 11, wherein the filtering means has an effective filter surface in the range of from about 0.2 to about 2 square meters, a length in the range of from about 10 to about 60 cm, a mean pore diameter in the range of from about 0.2 to about 2 microns.

13. The process according to claim 11, wherein the filtering means has an effective filter surface in the range of from about 0.8 to about 1.7 square meters, a length in the range of from about 10 to about 50 cm, and a mean pore diameter in the range of from about 0.4 to about 1 micron.

14. The process according to claim 11, wherein the volumes of the filtering means with its inner core and the filter body approximately equal the volume of the cylindrical housing in which they are disposed, and the filtering means is centrally disposed within the filter body.

15. The process according to claim 11, wherein the housing defines an additional outlet in communication with the filter body for the passage of precipitate and a portion of the serum or plasma not passed not passed through the filtering means 16. The process according to claim 11, wherein the filter body and filtering means are the same length as each other and the cylindrical housing.

17. The process according to claim 11, wherein the process is conducted at the ambient atmospheric pressure, without the need for applying a pressure differential across the permeable filtering means.

18. The process according to claim 11, wherein the macromolecular pathological and toxic species is beta-lipoprotein.

19. A process for the selective exteracorporeal separation of precipitates of beta-lipoprotein from blood having serum and plasma constituents which comprises passing the serum or plasma through a filter candle disposed in a substantially cylindrical housing, said filter candle comprising a selectively permeable filtering means having an inner core in communication with a filtrate outlet and having a mean pore diameter in the range of about 0.2 to about 2 microns and an effective filtering surface in the range of about 0.2 to 2 square meters and which is longitudinally disposed within a filter body having an inlet and an outlet, through which filter body the serum or plasma is passed such that the serum or plasma enters one end of the filter body through the inlet and contacts the filtering means through which is passed filtrate excluding the precipitate, and the remainder of the plasma or serum, including the precipitate, is permitted to exit the filter body at the outlet thereof.

* * * * *

UNITED STATES PATENT AND TRADEMARK OFFICE
CERTIFICATE OF CORRECTION

PATENT NO. : 4,648,974

DATED : March 10, 1987

INVENTOR(S) : Gerhard Rosskopf, et al.

It is certified that error appears in the above-identified patent and that said Letters Patent is hereby corrected as shown below:

Column 1, line 27, delete "lipo-metabollic" and substitute therefor --lipo-metabolic--.

Column 2, line 57, delete the second "or".

Column 5, line 27, delete "patient" and substitute therefor --patient's--.

Column 5, line 53, between "resulted" and "a", insert --in--.

Column 6, line 33, between "which" and "included", insert --are--.

Column 6, line 34, delete "define", and substitute therefor --defined--.

UNITED STATES PATENT AND TRADEMARK OFFICE
CERTIFICATE OF CORRECTION

PATENT NO.   : 4,648,974
DATED        : March 10, 1987
INVENTOR(S)  : Gerhard Rosskopf, et al.

It is certified that error appears in the above-identified patent and that said Letters Patent is hereby corrected as shown below:

Column 6, line 39, delete "exteracorporeal" and substitute therefor --extracorporeal--.

Column 6, line 52, delete "means" and substitute therefor --mean--.

Column 7, line 37, delete "exteracorporeal" and substitute therefor --extracorporeal--.

Column 8, line 4, between "60 cm," and "a", insert --and--.

Column 8, line 22, delete the second "not passed".

Column 8, line 34, delete "exteracorporeal" and substitute therefor --extracorporeal--.

Signed and Sealed this

Twenty-first Day of March, 1989

Attest:

*Attesting Officer*

DONALD J. QUIGG

*Commissioner of Patents and Trademarks*